MINIATURE ROSE PLANT
Filed Nov. 5, 1975
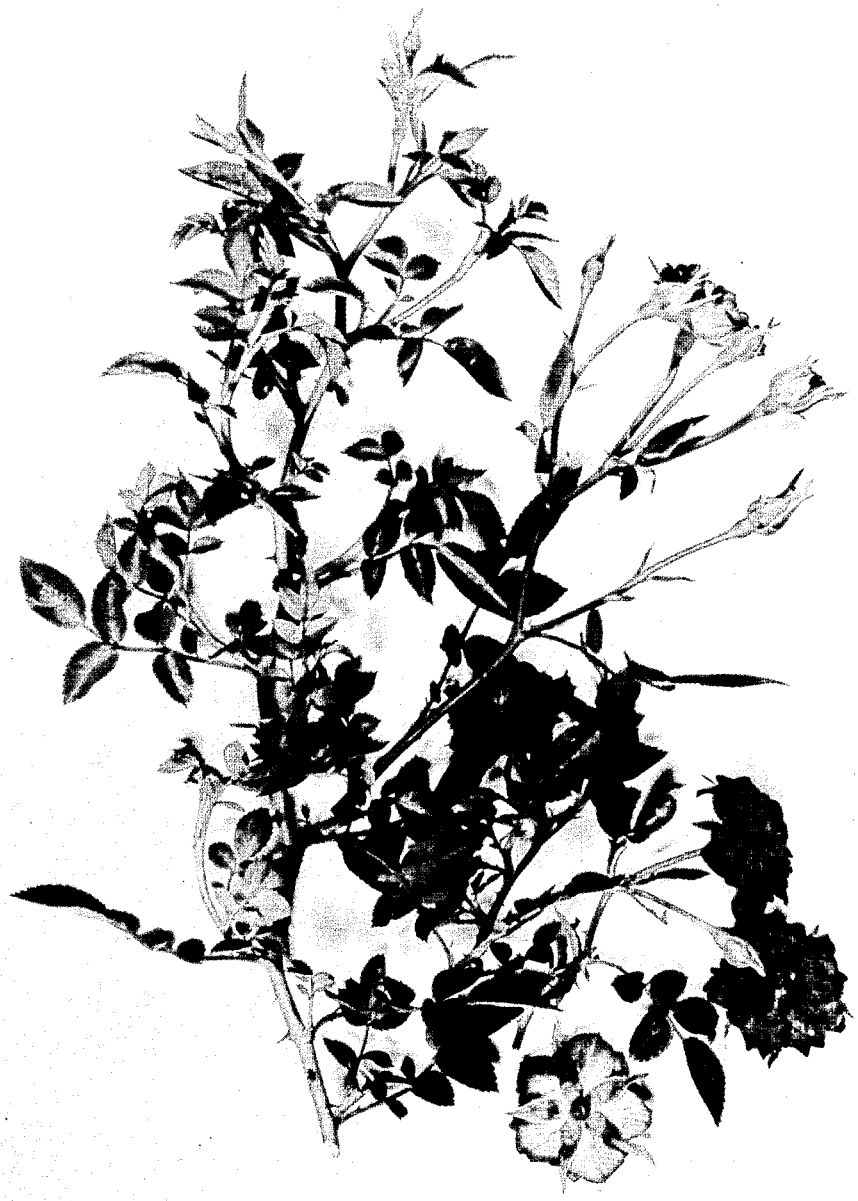

United States Patent

Plant Pat. 3,962

Patented Oct. 19, 1976

3,962

MINIATURE ROSE PLANT

Ralph S. Moore, 2519 E. Noble Ave., Visalia, Calif. 93277

Filed Nov. 5, 1975, Ser. No. 629,001

Int. Cl.[2] A01H *5/00*

U.S. Cl. Plt.—6 1 Claim

The present invention relates to a new and distinct variety of hardy, dwarf, rambling type of rose plant of the miniature class; the variety being primarily characterized—as to novelty—by the unique trailing or prostrate growth habit; by deep red buds and flowers which in general color effect are dark red when grown outdoors and almost the same deep red color when grown in greenhouse, and the constant repeat habit of flowering.

The variety is further characterized by:

An abundance of bloom, with flowers borne singly or several to stem in loose clusters.

Little or no fragrance.

A plant which is vigorous, of trailing or prostrate growth habit, semi-glossy (or matte) foliage with pointed leaflets; the flowers and foliage being similar in size to the variety My Valentine (miniature—U.S. plant patent applied for). The plant has a normal average height of 8 to 10 inches and a spread of 3 to 5 feet at maturity.

A plant which grows and blooms satisfactorily both in greenhouse and outdoors; is a good plant for growing in pots; hanging baskets or as a ground cover and provides excellent garden decoration as well as cut flowers.

The present variety of miniature rose was originated by me at my nursery located at Visalia, Calif., under conditions of careful control and observation, as a cross between an unnamed seedling (Rosa Wichuriana × Floradora—both unpatented) as the seed parent and Magic Dragon (Climbing miniature—not patented) as the pollen parent.

Subsequent to origination of the variety I successfully asexually reproduced it in my nursery located as aforesaid, by budding as well as by cuttings; the reproductions having run true in all respects.

Referring now specifically to the new and distinct variety of miniature rose plant, the following is a detailed description thereof in outline; all major color plate identification being by reference to the British Colour Council Horticultural Colour Chart, except where common terms of color definition are employed.

Type: Hardy; dwarf; trailing; seedling; outdoors; cut flowers garden decoration; hanging basket; ground cover.

Class: Miniature.

Flowers:

*Continuity.*—Continuous.

*Fragrance.*—Little or none.

Flowers borne: Singly and several together (3 to 5) on normal strength short to medium length stems.

Quantity of bloom: Abundant outside and less abundant in greenhouse.

Bud:

*Peduncle.*—Medium length; slender; erect; medium green sometimes tinted bronze (outdoors); very small short stiff hairs and sometimes some short prickles. Before calyx breaks, size—small. Form medium long; pointed, with few or no foliaceous appendages and few tiny short hairs on surface of the bud; with foliaceous parts extending beyond the tip of the bud equal to one-half or less of its length.

*Color.*—medium green, sometimes tinted bronze (outdoors). As calyx breaks, color—red. As first petal opens: Red, showing near-white at base of petal; size—small. Form: Medium length; pointed; cup shaped at first becoming rounded or high centered. Opening—opens well in all weather.

Bloom:

*Size when fully open.*—Small, averaging 25–28 mm. (about 1"). Petalage—very double—up to 40 (or more) petals (plus several narrow petaloids) arranged regularly.

*Form.*—cupped at first, with petals rolled loosely outward, and later at maturity becoming high centered with petals being loosely rolled outward.

Petals: Thick; satiny to velvetly inside and satiny outside. Shape—outside petals, oval (broad lanceolate with nearly round tip); intermediate, broad lanceolate with acute tip; inside, narrow lanceolate.

Color: Newly opened flower from a plant grown outdoors (June 1975) Visalia, Calif.:

*Outside petal.*—Outside surface—small near white area at base blending into Indian Lake 826/1 on lower ⅓ of petal then overlaid with much darker (blackish) color on upper ½ of petal; inside surface—white to near white area on base ¼ to ⅓ of petal, thence blending into a relatively narrow crescent shaped band of red similar to Rose Bengal 25, with the upper ⅔ overlaid with very dark (blackish) red.

*Intermediate petal.*—Outside surface—similar to outside petal but white area at base being relatively larger; inside surface similar to outside petal.

*Inner petal.*—Outside surface—similar to intermediate petal; inside surface—similar to intermediate petal.

*General color effect.*—Newly opened flower.—Rich deep red. Three days open—usually same red color. Behavior—spent petals or entire flower usually drops off. Flower color is very lasting even in warm weather. Flower longevity (September 1975)—plant in garden or pot—5–7 days or longer. Cut flowers at living room temperature—4 to 5 days or longer.

Reproductive organs:

*Stamens.*—Very few.

*Filaments.*—Medium length; near white.

*Pollen.*—Very little.

*Pistils.*—Moderate number.

*Styles.*—Even; medium length; bunched.

*Ovaries.*—All enclosed in calyx.

*Hips.*—None.

*Sepals.*—Permanent; spear shaped; usually remain against petals as flower opens; sometimes recurved.

*Seeds.*—None.

Foliage:

*Leaves.*—Compound of five leaflets (sometimes 7); abundant; small; leathery; semi-glossy.

*Leaflets.*—Shape: Lanceolate; apex acute; base rounded or rounded acute. Margin serrate. Color: Normal green; new growth often tinted bronze. Rachis: Medium strength; upper side, grooved, underside moderately thorny. Stiples: Medium length; narrow; short to medium length points, turning out at an angle of 45 degrees or more (sometimes less).

Growth:

*Habit.*—Dwarf; much branched, trailing.

*Growth.*—Free: vigorous.

*Canes.*—Medium; slender.

*Main stems.*—Color; dull green. Thorns: moderately thorny; medium length; nearly straight—color—gray. Prickles—few or none. Hairs—none. Branches—color: Medium green. Thorns: moderately thorny; short; nearly straight; short oval base. Prickles; none. Hairs—none. New shoots—

Color: medium green, often tinted bronze. Thorns: moderately thorny; short; nearly straight; Color—reddish; sharp points; base oval. Prickles: None.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, much branched, trailing type as illustrated and described, characterized by buds and flowers resembling the My Valentine miniature rose (patent applied for) in general size, form and red color (but slightly darker hue); and further characterized by a plant of vigorous, much branched trailing growth habit, easy to propagate from cuttings, with small semi-glossy (or matte) foliage and an abundancy of bloom produced recurrently throughout the growing season.

No references cited.

ROBERT E. BAGWILL, Primary Examiner